US006882423B2

United States Patent
Rust et al.

(10) Patent No.: US 6,882,423 B2
(45) Date of Patent: Apr. 19, 2005

(54) APPARATUS AND METHOD FOR PRECISION TESTING OF FIBER LENGTH USING ELECTROSTATIC COLLECTION AND CONTROL OF FIBERS

(75) Inventors: Jon P. Rust, Cary, NC (US); Stephen P. Stroupe, Gastonia, NC (US); Thesley A. Byrd, Sanford, NC (US); Joseph A. Brenzovich, Apex, NC (US)

(73) Assignee: North Carolina State University, Raleigh, NC (US)

(*) Notice: Subject to any disclaimer, the term of this patent is extended or adjusted under 35 U.S.C. 154(b) by 249 days.

(21) Appl. No.: 10/347,907

(22) Filed: Jan. 21, 2003

(65) Prior Publication Data
US 2004/0141188 A1 Jul. 22, 2004

(51) Int. Cl.[7] .............................................. G01N 21/84
(52) U.S. Cl. ....................................................... 356/429
(58) Field of Search ................................ 356/429–431, 356/630, 614, 615, 634; 382/111, 141

(56) References Cited

U.S. PATENT DOCUMENTS

| | | | |
|---|---|---|---|
| 2,711,626 A | | 6/1955 | Oglesby et al. |
| 3,591,294 A | * | 7/1971 | Neil ............................ 356/147 |
| 4,040,243 A | | 8/1977 | Weller, Jr. |
| 4,468,922 A | | 9/1984 | McCrady et al. |
| 4,512,060 A | | 4/1985 | Shofner |
| 4,827,574 A | | 5/1989 | Nakano et al. |
| 5,054,317 A | * | 10/1991 | Laubscher ................... 73/160 |
| 5,167,150 A | * | 12/1992 | Shofner et al. ............... 73/160 |
| 5,327,617 A | | 7/1994 | Yao |
| 5,491,876 A | | 2/1996 | Shofner et al. |
| 6,717,675 B1 | * | 4/2004 | Munch ........................ 356/429 |

OTHER PUBLICATIONS

Ikiz, et al., "Fiber Length Measurement by Image Processing,".

* cited by examiner

Primary Examiner—Michael P. Stafira
(74) Attorney, Agent, or Firm—Jenkins, Wilson & Taylor, P.A.

(57) ABSTRACT

A system for precision testing of fiber length and the like using electrostatic collection and control of fibers. The system comprises two spaced-apart and longitudinal extending electrode plates wherein one electrode plate has a positive charge and the other electrode plate is grounded or has a negative charge. An endless rotating belt extends between and parallel to the electrode plates, and the rotating belt is positioned next adjacent and in contact with or in close proximity to one of the two spaced-apart electrode plates such that the distance between the belt and the other electrode plate is greater than the length of fibers to be tested. A fiber introduction system is provided to introduce a plurality of individual fibers above the two electrode plates such that the fibers will adhere to the belt and the other ends of the fibers are attracted to the other electrode plate and thereby straightened. An imaging system is provided above the belt to generate image data corresponding to the length of individual fibers being transported by the rotating belt, and a data processor serves to analyze the image data to determine the length of fibers passing beneath the imaging system.

22 Claims, 9 Drawing Sheets

APPARATUS AND METHOD FOR PRECISION TESTING OF FIBER LENGTH USING ELECTROSTATIC COLLECTION AND CONTROL OF FIBERS

FIELD OF THE INVENTION

The present invention relates generally to the testing of fiber samples and, more particularly, to precision testing of fiber length utilizing electrostatic collection and control of fibers during image analysis.

RELATED ART

Testing of fiber samples, such as, but not limited to, cotton, is important for determining the market value of a particular batch of material, as well as for determining a suitable usage and what processing may be required in gins or spinning mills. Today, nearly 100% of the cotton grown in the United States is classed employing testing instruments. Testing includes determining such characteristics as fiber length, as well as the content of undesired textile entities such as trash and neps.

As a relatively early example, a comb-like device for preparing a sample of ginned cotton for measuring the fiber length thereof is disclosed in HERTEL U.S. Pat. No. 2,404,708, which issued in 1946. That same inventor later developed what is now known as HERTEL needle sampler, disclosed in HERTEL U.S. Pat. No. 3,057,019. The HERTEL needle sampler is a comb-like device arranged for movement past a perforated plate which has a fibrous mass pushed against the opposite side so that portions of the fibrous mass protrude through the perforations and are loaded into the needles. A screw-thread based locking device then retains the fibers on the needle sampler, forming what is known in the art as a tapered beard because the fibers are of varying lengths. The tapered beard is prepared by combing and brushing to parallelize the fibers, as well as to remove loose fibers. An automated version of the HERTEL needle sampler is contained within and is a major element of a fiber testing apparatus known as the Model 900A High Volume Instrument (HVI). This apparatus has been manufactured by Spinlab, Inc., but is now manufactured by Zellweger Uster, Inc. in Knoxville, Tenn.

The tapered beard is then subjected to analysis after preparation. For example, an instrument known as a Fibrograph, formerly manufactured by Spinlab, Inc., and now by Zellweger Uster, Inc. in Knoxville, Tenn., is employed to optically determine various characteristics of the tapered beard, including the profile along its length. In addition, a separate test may be made of the strength of the tapered beard.

In some respects, the sample as taken by a HERTEL needle sampler and the measurement of length and strength therefrom, are worldwide standards.

The approach just described involves collectively testing, essentially simultaneously, all of the fibers of a sample, assumed to be a representative sample. An alternative approach is to individualize and test single fibers and other textile entities, for example neps and trash. Testing single fiber entities can provide a better analysis. Thus, measuring directly, and at high speed, physical properties of single entities in a fiber sample results in basic measurements which provide more and better information which is necessary in modern textile manufacturing. The measurements are more basic because single entities (single fibers, single neps, single trash particles, single microdust particles, etc.) are directly measured rather than indirectly by measuring bulk or bundle properties. Equally importantly, they are more basic because statistical distributions are easily formed with the aid of modern electronics technology.

However, such an approach requires means for individualizing single entities and feeding them one at a time into suitable analysis means for testing. A device for such isolation can be generally termed a "fiber individualizer", and is generally so termed herein, although a more precise term is "entity individualizer" since, for purposes of testing, it is necessary to accurately determine the amount of neps and trash in a particular sample, in addition to characteristics of the fibers themselves.

An example of such single entity testing apparatus is disclosed in Shofner U.S. Pat. No. 4,512,060, which discloses what is termed in that patent a microdust and trash machine (MTM), and what has since become known as an Advanced Fiber Information System (AFIS). The machine is currently manufactured by Zellweger Uster, Inc. in Knoxville, Tenn.

In one form, the AFIS machine separates fibers and neps into one airstream, and trash into another air stream. Optical-based sensors then measure the individual entities. Individual entities can be analyzed at rates as high as 1000 per second. An AFIS machine more particularly includes an aeromechanical separator or fiber individualizer; high speed single entity sensors; and a high information rate computer for data collection and analysis.

Improvements to the AFIS, particularly improved sensors where a single sensor analyzes neps, trash and fibers individualized all in one air stream are disclosed in Shofner, et al U.S. Pat. No. 5,270,787 entitled "Electro-Optical Methods and Apparatus for High Speed, Multivariant Measurement of Individual Entities in Fiber or Other Samples", and Shofner, et al. U.S. Pat. No. 5,469,253 entitled "Apparatus and Method for Testing Multiple Characteristics of Single Textile Sample with Automatic Feed."

The fiber individualizer portion of an AFIS, such as is disclosed in previously referenced U.S. Pat. No. 4,512,060, includes a cylindrical rotating beater wheel having projections which engage fibers of fibrous material fed to the beater wheel for testing. The beater wheels rotates at typically 7,500 rpm, with a circumferential velocity of 5,000 FPM, and is similar to the licker-in of a conventional carding machine, or the beater stage of an open-end spinning head, with the exception that the AFIS beater wheel includes perforations which allow radially inward airflow.

One well known disadvantage of the device disclosed previously in U.S. Pat. No. 4,512,060 is accuracy and precision of fiber length measurement. This is due in part to the tendency of the device to sometimes measure two partially overlapping fibers as one, and the inability of the device to distinguish whether a fiber is doubled over upon itself or straight. As a result, tens of thousands of fibers must be measured in order to obtain data which, although somewhat reproducible, has been shown to have questionable accuracy.

Thus, there remains a need for a highly precise machine to individualize and analyze the length et al. of fibers. Applicants have developed such a machine.

SUMMARY OF THE INVENTION

The present invention is an apparatus and method to control individual fibers with high precision to develop highly accurate data about fiber length. The function of the apparatus is to take the individualized airborne fiber, gain control of each fiber, and present each fiber in a fashion that can be utilized by an imaging system. Parts of the apparatus include: a high resistance platform, two metal electrode plates that face each other, high resistance supports for the electrode plates, a high voltage power source, a high resistance belt, a precision motor and pulleys to support the belt. The most common shape of the electrode plates is going to be generally a rectangle with the length being significantly greater that the height of the plate, and the thickness and profile is unrestricted but is to be preferably small in comparison to the height and length. The electrode plates are to be positioned so that the length runs parallel to the platform, the height is perpendicular to the platform, and the faces of the electrodes are parallel to each other.

Also a part of the apparatus is a direct current high voltage source that produces a voltage potential. To one electrode plate the positive terminal of the high voltage source is to be connected, and to the opposing electrode plate the grounded or negative terminal is to be connected. The air space between the electrode plates is to be of such a high resistance that the current between the plates should be close to nonexistent. Since the high voltage is DC, an electrostatic field will have been created going from the positive terminal plate to the grounded or negative terminal plate. Attached to the other side of the electrode plates are support structures. The support structures are to be made of a high resistance material. This serves to isolate the areas of high voltage so that short circuits will not occur to disrupt the electrostatic field, and to minimize the risk of damage to other components and technicians resulting from the high voltage.

The faces of the electrodes are to have no obstructions between them except a rotating endless belt. The belt may be an electrical conductor. However, fibers will dwell on the belt longer if the resistance of the belt is high. Therefore, generally, the belt is to be made of a high resistance material, and is opaque and non-reflective so that light cannot pass through it. The belt extends farther than the length of the electrode plates, the belt width is kept to a minimum (preferably 0.001 inch–0.50 inch) and the belt thickness is relatively thin so that all fibers in contact with the side of the belt remain in focus. The belt length is to run along the length between the electrode plates, and the width is to be perpendicular to the electrode plates. Placement of the belt is such that it is approximately equidistant from both the top and bottom of the plates, and the edge of the belt is positioned to come into slight contact with or close proximity to one electrode plate (the negative plate). The distance between the opposite edge of the belt and the opposing electrode plate is to be greater than the longest possible length for any fiber being tested. Belt length is to extend far enough beyond the lengths of the plates so that pulleys can be positioned so that the belt can be extended around them.

Each of the pulleys is to be low conductive in nature, and will not contact the electrode plates or any other material with a high voltage. The two pulleys are to be kept tight enough to prevent any slack in the belt, but do not have to be excessively tight since a minimum of load is to be placed on the belt. One pulley is to be placed on an axle, and is to let the belt move freely along with the pulley around the axle. One pulley is to be attached to a motor. The motor is to be used to control the speed of the belt as it moves from one end of the electrode plate to the other. The motor, support structures, and any other material that risks being conductive to the high voltage must be grounded.

The apparatus uses the electrostatic field to control the orientation of the fibers, and the belt's movement is used to move the fibers through the electrostatic field. Since electrostatics are involved it is very imperative that the humidity and temperature be controlled in order to control the moisture content in the fiber. Once fibers are introduced to the apparatus they are allowed to enter a state of free fall in the air. A combination of chutes and air currents guide the individualized airborne fibers into the space between one end of the electrode plate pair. There the electrostatic field creates a change in the charge on the fiber. Instantly the fiber gains an induced charge, and is immediately attracted to one of the plates. Once the fiber comes into contact with the surface of the electrode plate, the charge characteristics of the fiber change. The fiber is then attracted to the opposing plate, and once it makes contact with its surface, the charge characteristics change again, and the fiber moves to the other electrode plate.

This behavior of the fiber bounding between electrode plates continues until the fiber comes into vicinity of the belt. Once the fiber comes close to the belt, one end of the fiber will adhere to the side of the belt that is facing the opposite or positive plate. The other end of the fiber will be attracted to the opposing electrode plate, and this attraction extends the fiber from the side of the belt to a point very close to the opposite electrode plate. The end result is a fiber that is stretched out (the fiber will be in the same plane as the belt). In this state the fiber is motionless relative to the belt, and its position is temporarily fixed relative to the belt. If the belt is composed of a more conducting material, the fibers will jump to the opposing plate more readily than if the belt is composed of a less conducting material. Then as the belt moves, it will carry along the fibers in their fixed positions, and allow them to be brought to the area of view of a vision system. At the far end of the electrode plates, a strong but highly localized suction system will remove the individual fibers off the belt and out of the apparatus so that no fiber can be measured twice. The apparatus including the fiber introduction system, electrode plates, endless belt, vision system and suction system are all controlled by a suitable computer which is programmed to analyze the images from the vision system to develop highly accurate fiber length data.

Therefore it is an object of the present invention to provide an improved system for collecting and delivering straightened individualized fibers to an imaging system for testing purposes.

It is another object of the present invention to provide an improved system for collecting and parallelizing fibers for feeding to a digital imaging device and related computer for more precise measurement of fiber length.

It is still another object of the present invention to provide a system for collecting and parallelizing fibers for presentation to a digital imaging device or other direct measurement device for obtaining a true and accurate measurement of fiber lengths from a fiber sample.

It is still another object of the present invention to provide an apparatus and method that utilizes an electrostatic field to straighten and then move fibers into the area of view of an imaging device in a manner that provides greater fiber length measurement accuracy than has heretofore been possible.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description, taken in connection with the drawings described in detail below.

DETAILED DESCRIPTION OF THE INVENTION

I. General Description

Referring to FIGS. 1–8, a good overview of the behavior of the apparatus, general designated 10, and the sequence of actions for individual parts can be developed. A fiber F, which has been individualized by a combing roll C, is directed by means of a feed chute 12 into the apparatus 10. As the airborne fibers F float down they come into the region between two opposing electrode plates 14A, 14B. The two opposing electrode plates have an electrostatic field between them that creates an induced charge on the fiber. As the fiber moves downward it becomes attracted to a belt 16, which is driven by a motor 18 connected to pulleys 20B. As the movement of belt 16 continues onward it takes the fiber F along with it until it reaches a region of image taking. At this place between the two opposing electroplates a light source 22 is projected upward from underneath belt 16. Light source 22 creates a back lighting condition for the fibers F in this region, and allows a camera 24 or other image-taking instrument placed above the belt to take the image of the fiber. As the fiber F moves past the region of the belt 16 it eventually comes under the influence of a suction device 26 that removes the fiber from off of belt 16. In this sequence of events everything is occurring simultaneously with different individualized fibers coming down chute 12, entering the electrostatic field, moving along the belt 16, having an image being taken of them, and being removed by suction device 26. In this manner a continuous stream of fibers can be passing through apparatus 10 at the same time, and a large number of fibers F can be imaged in a short period of time.

By looking at FIGS. 2–7 of apparatus 10, it is possible to see the behavior of all the components. By looking at apparatus 10 from this perspective it is possible to see the behavior of an individual fiber F as it goes through apparatus 10. In this view, both positive electrode plate 14B and grounded or negative electrode plate 14A can be seen. In this design, the position of positive electrode plate 14B and grounded or negative electrode plate 14A can be switched. A significant voltage potential exists between the two plates (5,000 to 100,000 volts or more), and a distance exists between the two plates that is greater than the sum of the width of the belt 16 and the length of the longest fiber F being measured. Since there is no physical connection between two plates 14A, 14B, an electrostatic field extends from one plate to the other. Running along side the grounded or negative electrode plate 14A is belt 16. Belt 16 just barely makes physical contact with the grounded or negative electrode plate 14A, extends out perpendicular to grounded or negative electrode plate 14A, and its other side is facing positive electrode plate 14B. Belt 16 moves along the length of electrode plate 14A from where fibers F are inserted into apparatus 10 to the area above light source 22. When fibers are first inserted into apparatus 10, they gain a charge and move very rapidly from electrode plate to electrode plate. When these unsettled fibers F move downwards near belt 16, one of their ends will adhere to the side of belt 16, and the electrostatic field will extend the other end of fiber F out towards positive electrode plate 14B. When this happens fibers F become settled and maintain a constant shape as they adhere to belt 16 and extend out.

The movement of belt 16 will cause fibers F to move along with belt 16 while maintaining their constant shape. Eventually fiber F will approach an area between two plates 14A, 14B that is above light source 22. At this point light is emitted from beneath the fiber, and this creates an image where the fiber is a shadow against a bright background. A camera 24 or other image taking device positioned above light source 22 can collect these images. As the fiber moves farther along, it exits the region between two electrode plates 14A, 14B, and loses most of its charge since it is no longer under the effect of the electrostatic field. At this point, suction device 26 is placed where it can remove fiber F from apparatus 10. Belt pulley 20B is attached on its back side to the shaft of motor 18 or other motor like device which has the ability to precisely control its rotational speed. As pulley 20B rotates, it provides a frictional force to belt 16 that controls the movement of belt 16. Since the pulley's speed is precisely controlled, the speed of belt 16 can also be precisely controlled. Belt 16 moves from pulley 20A to 20B along the path of electrode plate 14A. Since both pulley 20B and belt 16 are made of highly resistive material, the amount of current that can flow through belt 16 from its contact with electrode plate 14A can be minimized.

Figure 1:
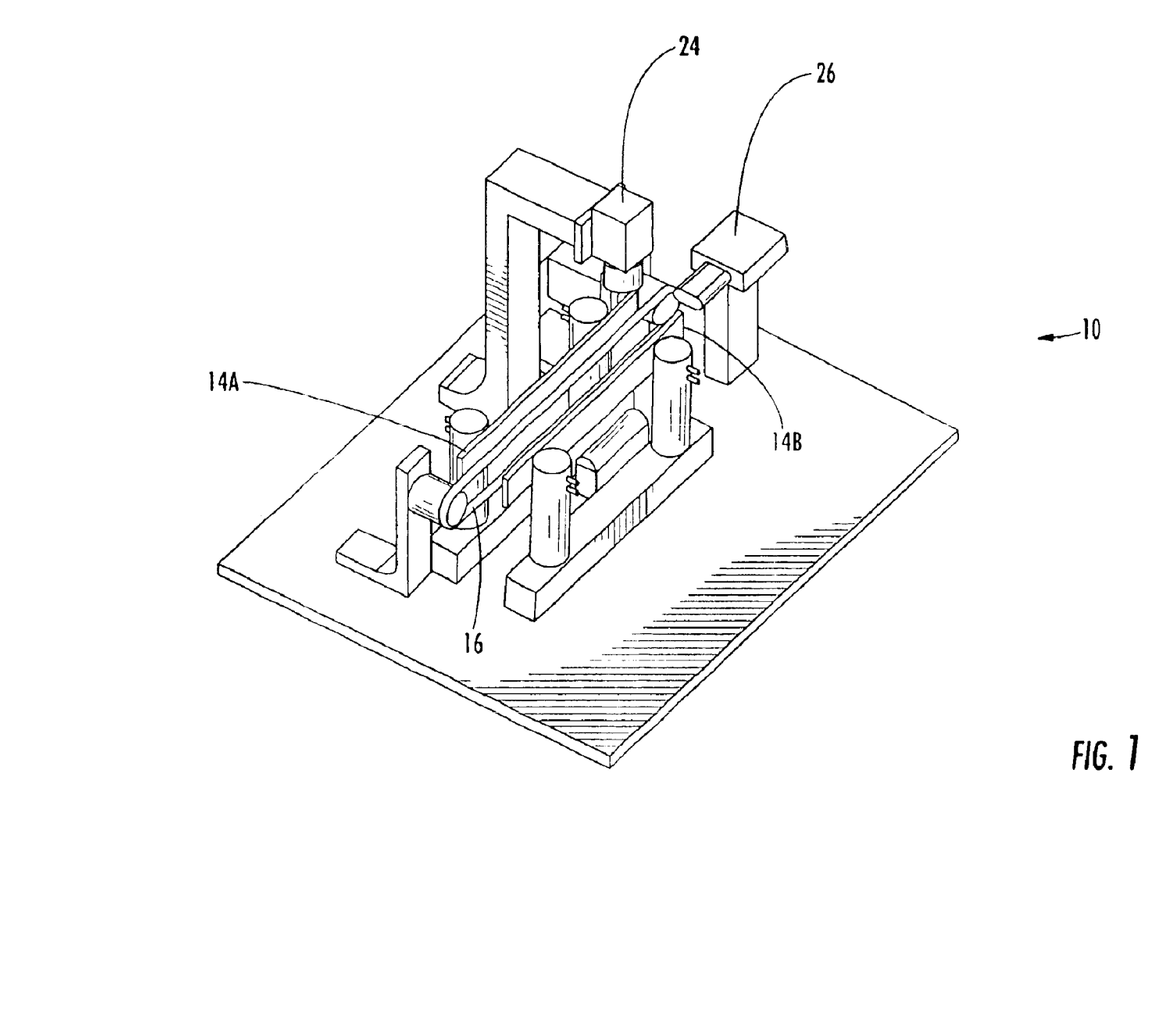
FIG. 1 is an isometric view of the fiber length measurement apparatus in accordance with a preferred embodiment of the invention.
Figure 2:
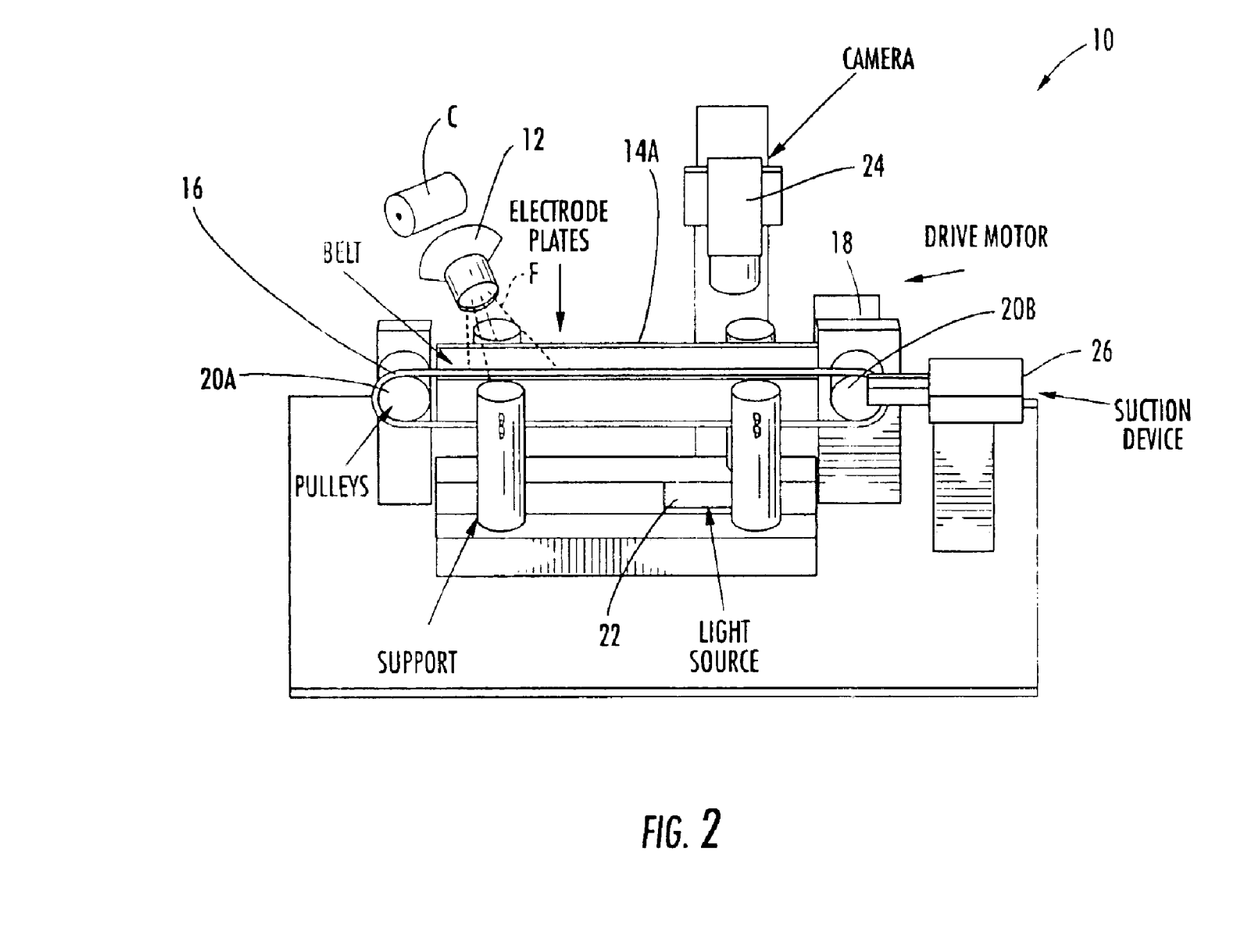
FIG. 2 is a side elevation view of the fiber length measurement apparatus shown in FIG. 1.
Figure 3:
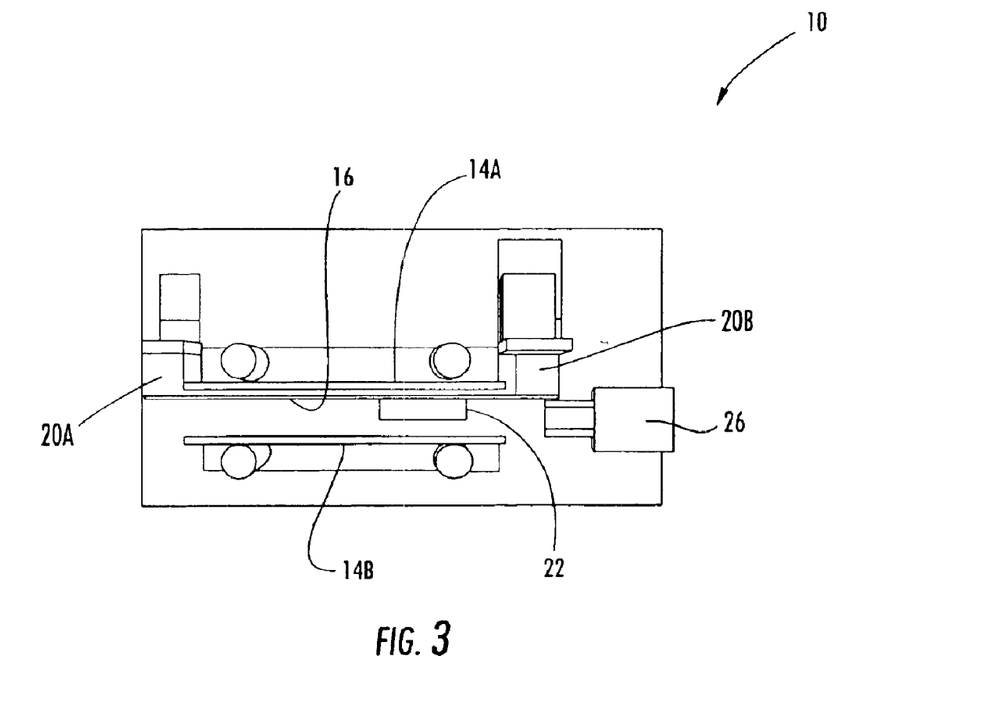
FIG. 3 is a top plan view of the fiber length measurement apparatus of the present invention.
Figure 3A:
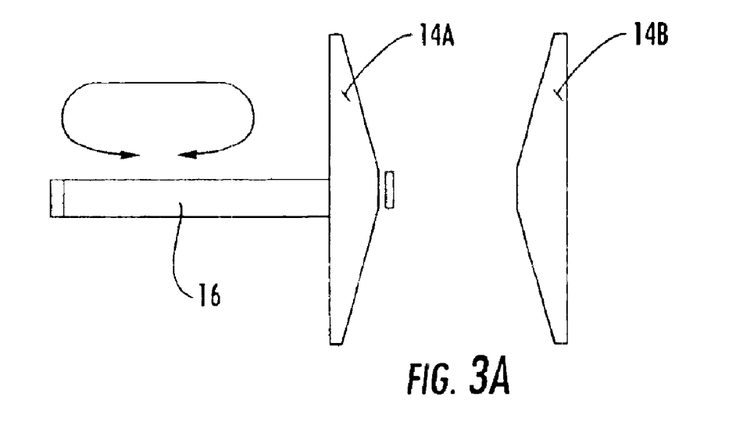
FIG. 3A is a vertical cross section view of the electrode plates with an alternative belt pathway extending therebetween.

After the fibers have been removed from the belt, the belt then can return to the end of the plates where the fibers are being fed by passing under the plates as shown in FIGS. 1, 2, 3, and 4 or by passing behind a plate (as shown in FIG. 3A) depending on whether the wider dimension of the belt is perpendicular to the height of the plate (as shown in FIGS. 1–7) or parallel to the height of the plate respectively (see FIG. 3A). Also, alternative plate designs include modifications to the rectangular cross-section shown in FIGS. 1, 3, 3A and 7. These may also include embodiments where the belt traverses, wholly, or in part, within a slot S cut into the plate (as shown in FIG. 5B).

II. Function of the Electrostatic Field

Figure 4:
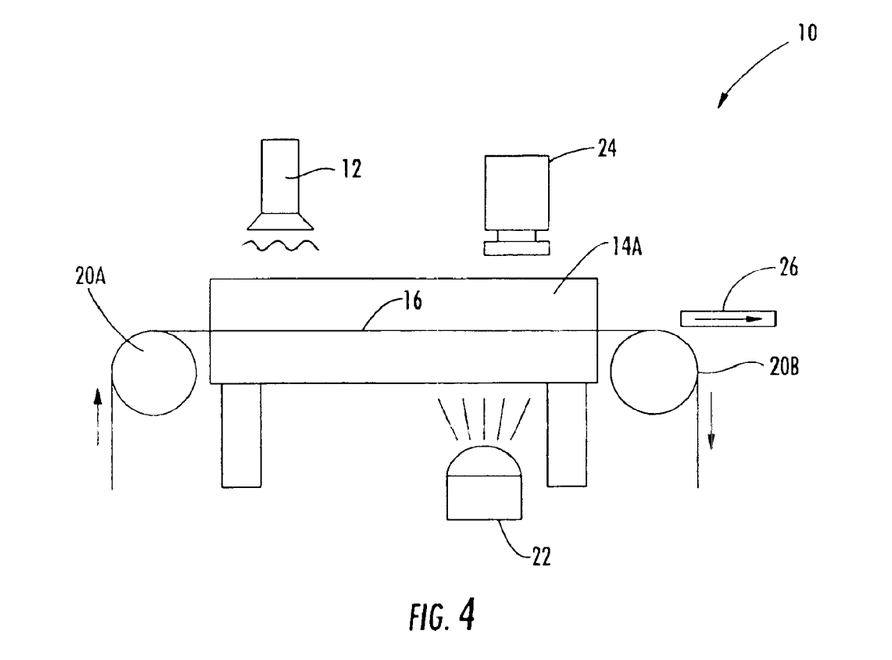
FIG. 4 is a schematic view of the fiber length measurement apparatus of the present invention.
Figure 5:
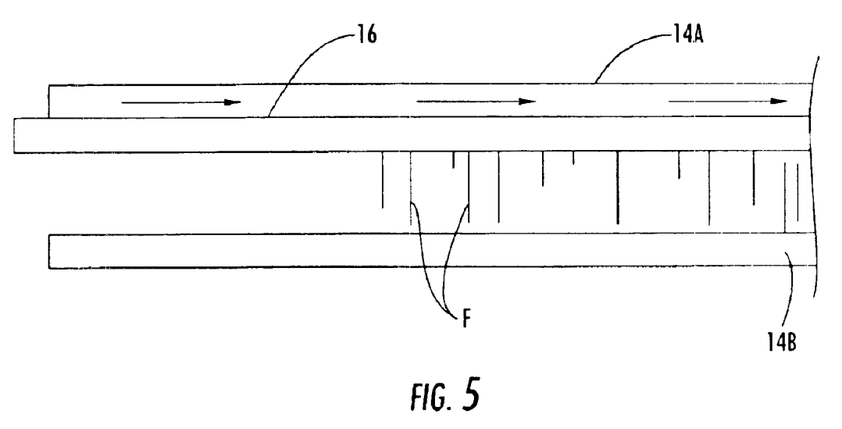
FIG. 5 is a top plan view of the region between the electrode plates of the fiber measurement apparatus of the present invention.
Figures 5A, 5B:
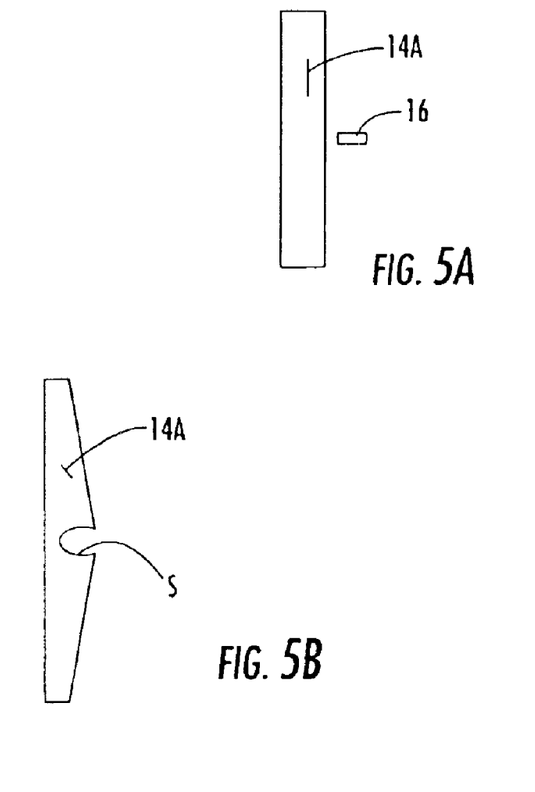
FIG. 5A is a vertical cross section view of electrode plate 14A in FIG. 5.
FIG. 5B is a vertical cross section of an alternative embodiment of electrode plate 14A in FIG. 5 having a slot therein for at least a portion of belt 16 to travel within.
Figure 6:
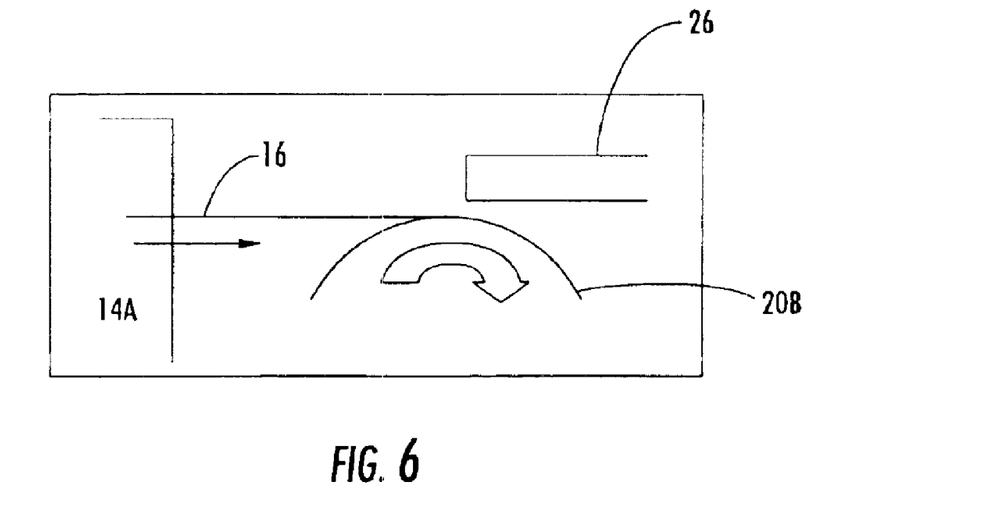
FIG. 6 is an enlarged and partial schematic view of the pulley and suction mechanism at the distal end of the belt of the fiber length measurement apparatus of the present invention.
Figure 7:
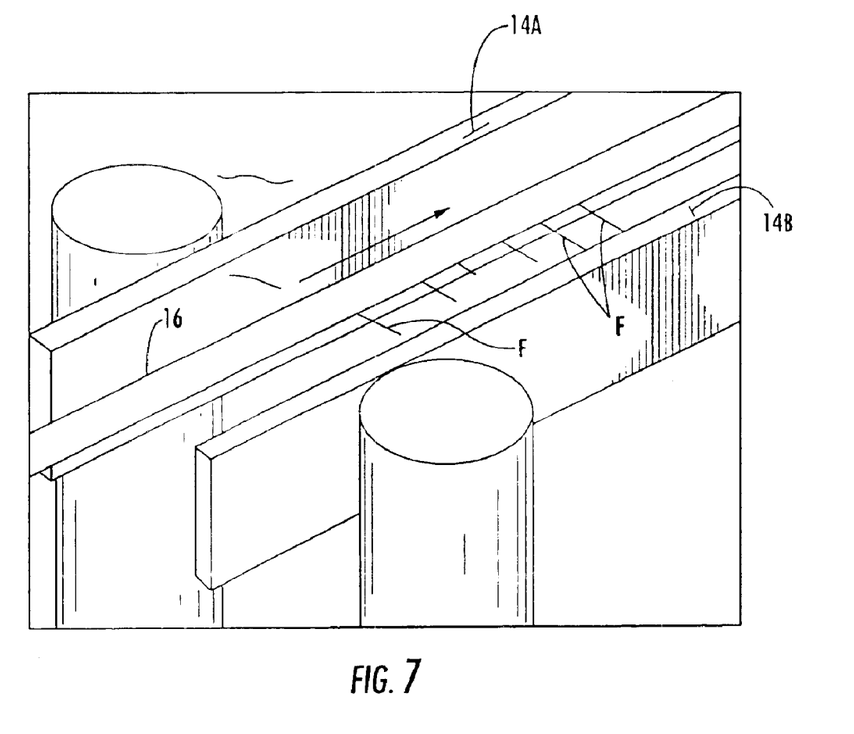
FIG. 7 is an isometric view of the proximal end of the belt of the fiber length measurement apparatus of the present invention showing the relationship of the belt to the two (2) spaced-apart electrode plates.

In FIGS. 2 and 4 we have the view of electrode plates 14A, 14B as if you removed electrode plate 14B, and obtained a side view of plate 14A. Electrode plate 14A is the plate that is in physical contact with or in close proximity to belt 16. Also in this drawing belt 16 runs the length of electrode plate 14A as it runs from the left to the right. An individualized, airborne fiber F is floating down towards the fiber controller by means of chute 16 that goes to the region between electrode plates 14A, 14B. The fiber F first floats down into the region at one end of electrode plates 14A, 14B. Once between the plates, the electrostatic field creates an induced charge on fiber F. The fiber will immediately be attracted to one of the plates, and move towards it. Once the fiber comes in contact with the plate, the electrostatic properties of the fiberwill change. Then the fiber will become attracted to the opposite electrode plate, and move towards it.

Once there, a change in electrostatic properties will again change, and the movement towards the opposite electrode plate will once again occur. These sequences can occur several times depending on the rate of descent for the fiber, fiber size, fiber moisture content, humidity, and the intensity of the electrostatic field. Once the fiber is adhered to belt 16, a change in the fiber's behavior will occur. At this point, one tip of the fiber will be attracted to opposite electrode plate 14B. This will cause the fiber to extend out with one tip attached to the side of belt 16, and the other tip extending out toward plate 14B (see FIG. 5). When this happens the tip attracted to the opposite plate is in mid-air, the fiber is straightened out, and is in the same plane as belt 16.

The fiber will maintain this shape as long as the electrostatic field is maintained between electrode plates 14A, 14B, and the fiber will not move relative to the belt 16. But since the belt is moving relative to electrode plate 14A, the fiber will move also relative to electrode plate 14A. The fiberwill move down the midsection of electrode plate 14A, and the time it takes the fiber to move along this region of the plate gives time for the fiber to settle and be fully extended. This region also gives spacing so the imaging system 24 can be placed away from fiber feed chute 12, and electrode plates 14A, 14B. Once the fiber moves toward the end of the electroplates, its shape will be fixed, it will be straightened out, and will be in the same focus plane as belt 16. In this region imaging device 24 focused into this region can take images of the fiber, and since new fibers F are continually being moved through this area new images can continually be made.

This system will have the fiber moving along belt 16 by means of a pulley. As the fiber leaves the proximal region between electrode plates 14A, 14B, the fiber will no longer be under the influence of the electrostatic field, and will no longer maintain a strong induced charge. When this happens the fiber will have a slight attraction to belt 16 but it will not be a very strong bond. As the fiber moves further from the proximal end of electrode plates 14A, 14B an air current runs over fiber F. The air current comes from suction device 26 at the end of belt 16 (see FIG. 6). Once a fiber gets close enough to suction device 26 the fiber will be drawn from belt 16 and into suction device 26. Through this means fibers are removed from apparatus 10 and not allowed to clutter the system. Removing the fiber from the system also prevents them from being measured twice.

Summarily, two electrode plates 14A, 14B extend in parallel and spaced-apart relationship with the electrostatic field between them. Running along the side of plate 14B in contact with or in close proximity thereto is a continuously running belt 16. Fibers F that are individualized and airborne by combing roll C are delivered to the proximal end of plates 14A, 14B by chute 12. Eventually a fiber falls down to the region between the plates. At this point the fiber becomes under the influence of the electrostatic field, and gains an induced charge. The fiber will rebound back and forth between plates 14A, 14B until it comes into contact with belt 16. At this location the fiber will adhere to the edge of belt 16. This end will stay adhered to the edge of belt 16 and the other end of the fiber will reach out to opposite electrode plate 14A. This action will stretch out the fiber from belt 16 to the electrode plate. The fiber will maintain this locked shape and will move along with the belt. The end result, if a steady stream of individualized fiber comes into the system, is a series of fibers that are all straightened out and transported down the length of electrode plate 14B to camera 24.

III. Details of Construction and Methodoloqy of Use

A computer PC is central to the control system of apparatus 10 and is vital to controlling all mechanisms, camera communication and acquisition, image analysis, report generation, and user interfacing. The computer is preferably equipped with a 1.67 Gigahertz processor, 512 megabytes of RAM, and a 60 gigabyte hard drive, or better.

Figure 8:
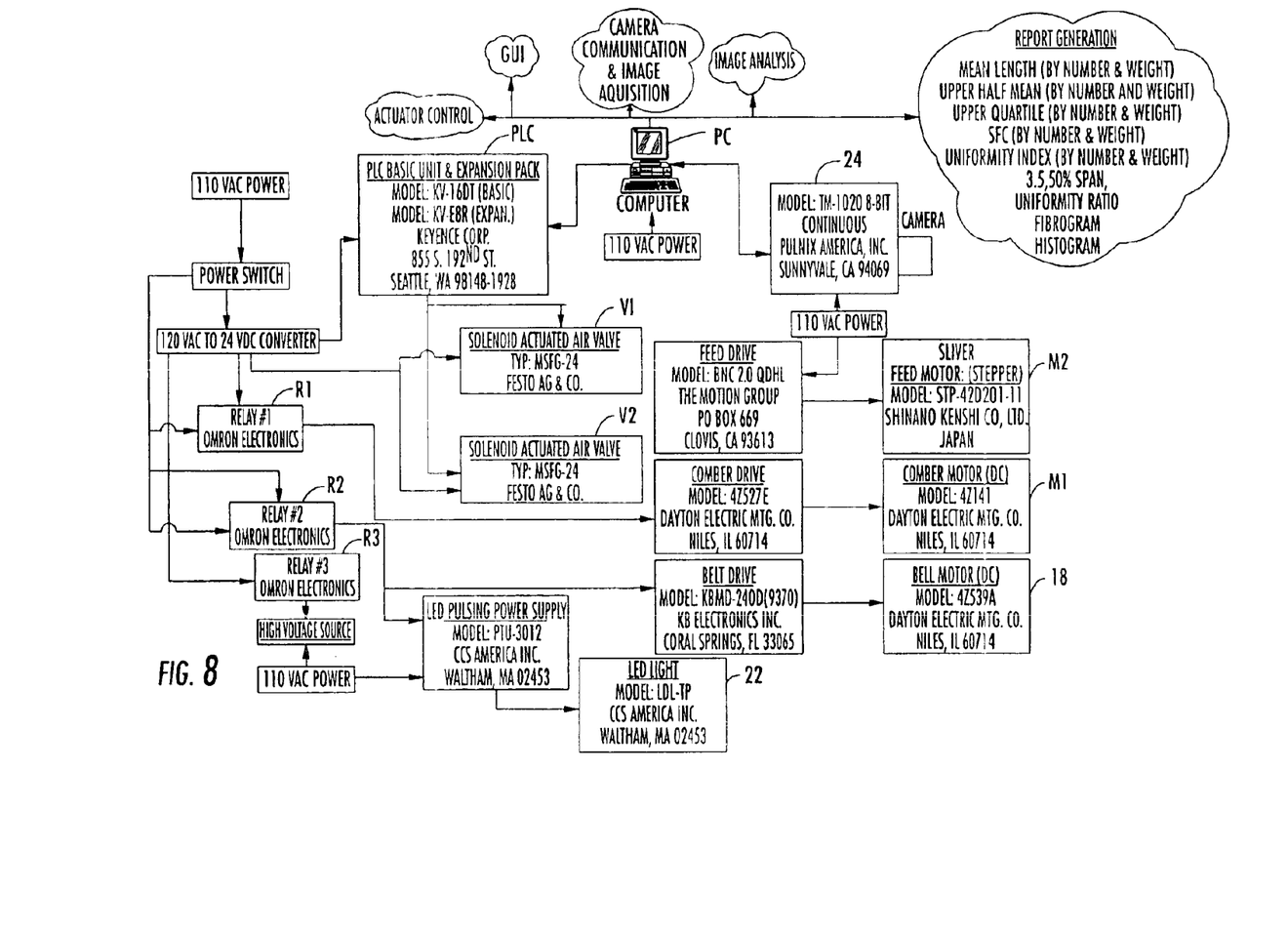
FIG. 8 is a schematic view of the components and circuitry of the fiber length measurement apparatus of the present invention.

Referring to FIG. 8, upon initiation of the apparatus through a graphical user interface (GUI), the computer sends a signal to a PLC, which is powered by a 24-Volt DC Power Supply. The power supply acts as a 120-Volt AC to 24-Volt DC converter used also to power other system components including two solenoid actuated air valves V1, V2 and three relays R1, R2, R3. Once signaled by the computer, the PLC activates and deactivates the three OMRON relays and the two solenoid actuated air valves in a timed manner to control electrical current to the pulsing LED power supply, high voltage power source, air suction devices, and motors of apparatus 10.

Relay number one is used to control the on/off status of the comber roll C for introducing fiber into chute 12. The 110-Volt AC from an electrical outlet is connected to relay number one through a power-switching device. The power from the outlet is used to provide power to the DC drive, which in turn powers the motor M1 for the friction-driven comber roll C. The range of speeds for the comber roll can be varied between 1,000 and 10,000 rpm.

Relay number two performs the function of controlling the on/off status of the belt motor 18 and the power supply for the backlight source 22, an array of pulsing light emitting diodes (LED's). The 110 Volt-AC power necessary to power belt motor 18 is connected to the OMRON relay through a switch. This 110-Volt AC powers the DC drive, which in turn drives DC belt motor 18 and belt 16. The range of linear speeds for belt 16 in apparatus 10 can be varied from 1 to 20 inches per second or more. In addition, this 110-Volt AC provides power to the LED array power supply, which is responsible for controlling the intensity and pulsing of LED light source 22.

Relay number three is responsible for controlling the on/off status of the high-voltage source (operating range from 5 to 100 thousand volts or more), which receives its power from a 110-Volt AC power strip. Also receiving power from the power strip is a stepper motor drive which controls the sliver feed rate into apparatus 10 through a stepper motor M2. This drive is also connected to the PLC, which controls its on/off status and the rate of pulses supplied to the motor. During normal processing, this pulse rate can range from 0.1 to 1 hertz and from 50 to 200 hertz during the system purging process.

For image acquisition and analysis, the computer is also in constant interaction with a PULNIX TM-1020 8-bit continuous camera 24. The computer PC prompts the frame grabber (manufactured by Engineering Design Team), which is installed in the computer, to receive an image for analysis after the previous image has been analyzed. After receiving an image, software installed on the computer recognizes belt 16 to be darker than any other existing object in the image and then proceeds to strip belt 16 from the image causing it to take on gray levels similar to that of the background. The software then applies a threshold to the image in such a manner that pixels containing fibers F are turned white, while the remainder of the pixels in the image is turned black. Next, the software scans a line fifty pixels from belt 16 in search of a white pixel. The scan can occur closer than 50 pixels from the belt or further away. As the distance between the scan line and the belt becomes greater, the chance of omitting a short fiber becomes greater. Upon reaching such a pixel the software proceeds to outline the perimeter of the white pixels, which represents a fiber F. After outlining is complete, the software proceeds with its scan across the image in search of fibers and continues until all fibers in the image have been outlined. The pixel-count around the perimeter of the fiber is then used to calculate the fiber length.

The calculated fiber lengths are passed into an array and a report is subsequently generated. The report contains a significant amount of fiber length information including fiber mean length, upper half mean length, upper quartile length, short fiber content, uniformity index, three adjustable span lengths, and the uniformity ratio. Also included in the report is a fibrogram and histogram of the fiber length data. Many other fiber length and length distribution statistics may be added to the reporting process as a matter of choice.

Each of the functions of apparatus 10 is performed at a specified time that is determined by the control software installed on computer PC. Once the desired number of fiber measurements has been obtained, apparatus 10 is prompted by the computer to proceed with purging and shutdown. The functioning sequence is as follows:

1. The apparatus begins at start-up by engaging the comber roll C, belt 16, and suction actuator (to remove fibers after measurement) as well as the light source and feed roll (with a slight delay to ensure the comber roll C is up to speed before inserting fiber). The feed roll speed is greater at this time than during image acquisition to ensure the sliver is fed into the system in a reasonable period of time and auxiliary suction is applied at this time to remove the large number of fibers being fed through the system during initial sliver feeding.
2. The apparatus then prompts the operator to insert the sliver.
3. Once the operator has acknowledged the insertion of fiber into the apparatus, the feed roll speed is reduced to ensure a suitable fiber flux into the fiber delivery area so that fibers are effectively individualized in the images. After a short delay to ensure the heavy fiber flux is purged from the comber roll C, the auxiliary suction is disengaged allowing the fibers to approach the plates and the belt.
4. With the belt, comber roll, feed roll, suction, pulsed illumination, and camera all operating, the system begins image acquisition and analysis.
5. The images are analyzed by the computer and image processing software until the desired number of fiber measurements is obtained at which time shut down proceeds.
6. Shut down begins with a prompt for the operator to remove the sliver from the feed area.
7. Once the operator has acknowledged that the sliver has been removed, the feed roll speed is increased and the auxiliary suction is engaged to run all remaining fibers through the system.
8. After 10 seconds (or after enough time to purge the system entirely of the fiber sample, depending on the specific mechanics) the feed roll is disengaged, followed by the comber roll C, belt 16, illumination device and lastly the suction mechanism.

Summarily, individual fiber lengths are measured by the disclosed system and any of an unlimited number of fiber length and fiber length distribution parameters can be calculated from the individual fiber length data. These fiber length and fiber length distribution parameters include but are not limited to: mean length (ML); upper half mean length (UHML); span lengths such as 2.5% span length; upper quartile length (UQL); short fiber content (SFS) by weight or by number; uniformity index (UI); and uniformity ratio (UR).

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. An apparatus for precision measurement of fiber length and fiber length distribution comprising:
    (a) two spaced-apart and longitudinally extending electrode plates wherein said plates have a significant voltage difference or potential between them;
    (b) an endless rotating belt extending between and parallel to said two electrode plates, said belt being next adjacent and in contact or close proximity to one of said electrode plates, and the distance between said belt and the other electrode plate being greater than the length of fibers to be tested;
    (c) a fiber introduction system to introduce a plurality of individual fibers such that one end of said fibers will adhere to said belt adjacent one of said electrode plates and the other end of said fibers will be attracted to the other of said electrode plates and thereby said fibers straightened;
    (d) an imaging system positioned above said belt to generate image data corresponding to the length of individual fibers being transported by said rotating belt between said two electrode plates; and
    (e) a data processor for analyzing the image data to determine the length of fibers passing beneath said imaging system.

2. The apparatus according to claim 1 wherein said one electrode plate has a negative charge and said other electrode plate is grounded.

3. The apparatus according to claim 1 wherein said one electrode plate has a positive charge and said other electrode plate is grounded.

4. The apparatus according to claim 1 wherein said one electrode plate has a positive charge and said other electrode plate is a negative charge.

5. The apparatus according to claim 1 wherein said one electrode plate comprises a longitudinally extending slot therein within which at least a part of said belt travels.

6. The apparatus according to claim 1 wherein said belt is relatively non-conductive.

7. The apparatus according to claim 1 wherein said belt is conductive.

8. The apparatus according to claim 1 wherein said belt is next adjacent and in contact with said grounded or negatively charged plate.

9. The apparatus according to claim 1 wherein said belt is next adjacent and in close proximity to said grounded or negatively charged plate.

10. The apparatus according to claim 1 wherein said fiber introduction system comprises a feed system for introducing a fiber sliver strand to said fiber introduction system and a comber roll for separating individual fibers from the fiber sliver strand for introduction above the proximal end of said two electrode plates.

11. The apparatus according to claim 1 wherein said imaging system comprises a digital camera.

12. The apparatus according to claim 11 including an array of pulsing light emitting diodes located beneath said digital camera and said belt to provide backlighting therefore.

13. The apparatus according to claim 1 wherein said data processor comprises a computer for processing said imaging signals to determine certain predetermined fiber length data.

14. The apparatus according to claim 13 wherein said computer controls the speed of said fiber introduction system and said rotating belt.

15. A method for precision measurement of fiber length and fiber length distribution comprising the steps of:
  (a) providing two spaced-apart and longitudinally extending electrode plates wherein said plates have a significant voltage difference or potential between them;
  (b) rotating an endless belt between and parallel to the two electrode plates wherein the belt is positioned next adjacent and in contact with or in close proximity to one of the electrode plates such that the distance between the belt and the other electrode plate is greater than the length of fibers to be tested;
  (c) introducing a plurality of individual fibers such that one end of the fibers will adhere to the belt adjacent one of the electrode plates and the other end of the fibers is attracted to the other of the electrode plates and thereby straightened;
  (d) generating image data from above said belt corresponding to the length of individual fibers being transported by the rotating belt between the two electrode plates; and
  (e) analyzing the image data with a data processor to determine the length of fibers passing between the two electrode plates.

16. The method according to claim 15 including positioning the rotating endless belt adjacent and in contact with said one electrode plate.

17. The method according to claim 15 including rotating the endless belt in a vertical pathway between said electrode plates.

18. The method according to claim 15 including rotating the endless belt in a horizontal pathway around said one electrode plate.

19. The method according to claim 15 wherein the plurality of individual fibers are introduced above the proximal end of the two electrode plates by feeding a sliver strand to a combing roll in order to individualize fibers from the sliver strand for introduction above the proximal end of the two electrode plates.

20. The method according to claim 19 including introducing the individualized fibers into a chute so as to direct them downwardly toward the proximal end of the two electrode plates.

21. The method according to claim 19 including imaging individual fibers being transported beneath the imaging system by the rotating endless belt.

22. The method according to claim 21 including analyzing individual fiber images with a computer and calculating fiber length data from an array of the individual fiber lengths with the computer.

* * * * *